United States Patent
Ahluwalia

Patent Number: 5,209,754
Date of Patent: May 11, 1993

[54] VAGINAL CERVICAL RETRACTOR ELEVATOR

[76] Inventor: Prabhat K. Ahluwalia, 4 Fowler Dr., St. Johnsville, N.Y. 13452

[21] Appl. No.: 862,371

[22] Filed: Apr. 2, 1992

[51] Int. Cl.$^5$ .................................. A61M 29/00
[52] U.S. Cl. ..................... 606/119; 606/108; 606/193; 606/1; 604/96; 604/101; 128/20
[58] Field of Search ............... 128/20, 774, 775, 778; 604/96, 101; 606/119, 193, 108

[56] References Cited

U.S. PATENT DOCUMENTS

| | | |
|---|---|---|
| 372,922 | 11/1887 | McCord . |
| 899,477 | 9/1908 | Williams ................ 606/119 |
| 2,400,251 | 5/1946 | Nagel ..................... 606/119 |
| 3,646,929 | 3/1972 | Bonnar .................. 606/119 |
| 3,777,743 | 12/1973 | Binard et al. ......... 606/119 |
| 3,877,433 | 4/1975 | Librach ................. 606/119 |
| 3,926,192 | 12/1975 | Van Maren . |
| 4,000,743 | 1/1977 | Weaver . |
| 4,976,717 | 12/1990 | Boyle . |
| 4,997,419 | 3/1991 | Lakatos et al. . |
| 5,104,377 | 4/1992 | Levine .................. 606/193 |

FOREIGN PATENT DOCUMENTS

| | | | |
|---|---|---|---|
| 0319394 | 6/1989 | European Pat. Off. .......... 606/119 |
| 2829118 | 1/1980 | Fed. Rep. of Germany ...... 606/193 |

Primary Examiner—Stephen C. Pellegrino
Assistant Examiner—Glenn Dawson
Attorney, Agent, or Firm—Hoffman, Wasson & Gitler

[57] ABSTRACT

A vaginal cervical retractor used to maneuver and visualize the uterus during various medical examinations and procedures would include an inner tube provided with a movable pair of plastic caps designed to be inserted into the uterine cavity. A cervical cap is secured to this tube to insure that the tube would not extend beyond a certain distance into the uterus. A hollow outer shaft is provided into which the inner tube can be inserted.

9 Claims, 5 Drawing Sheets

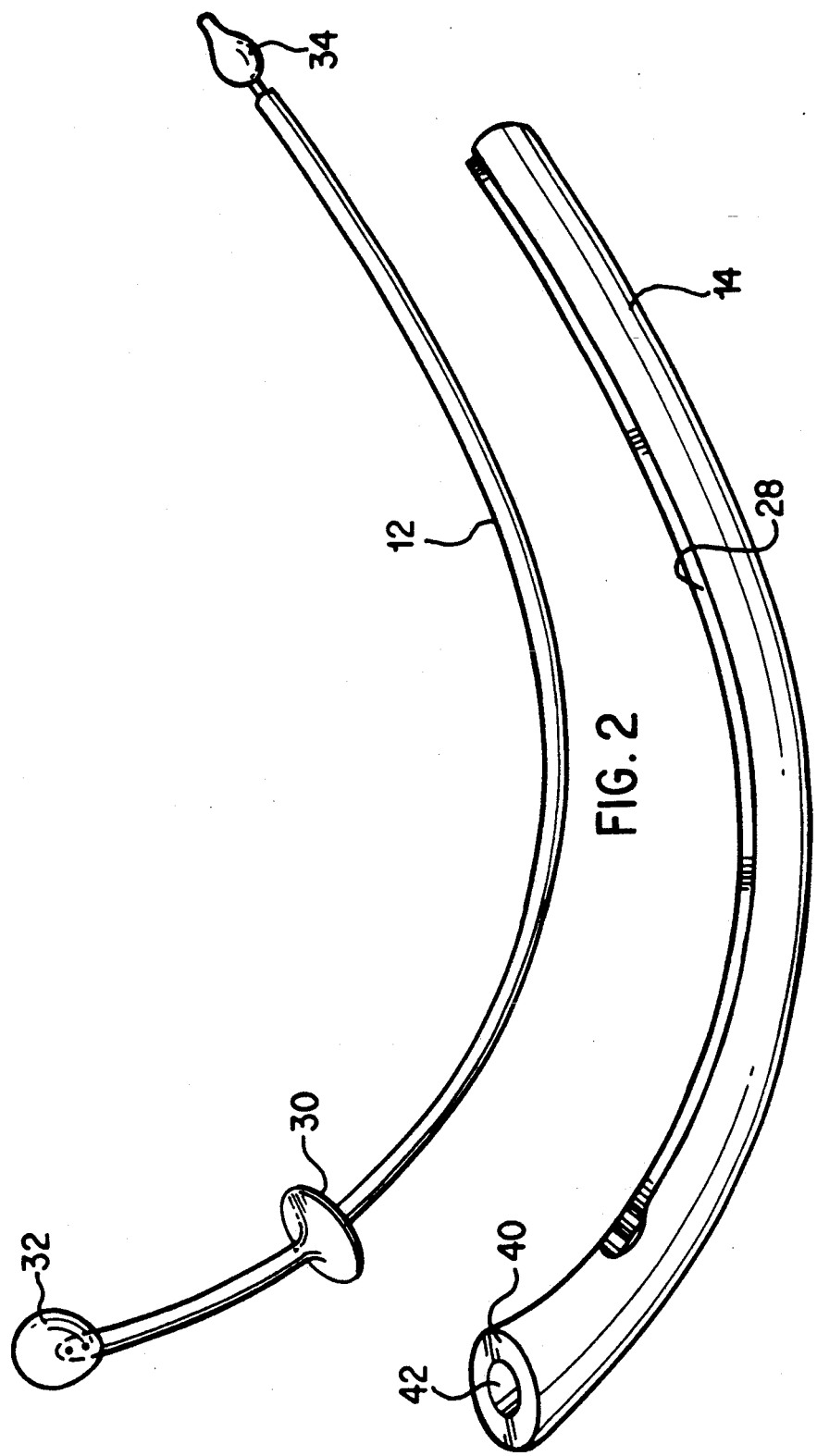

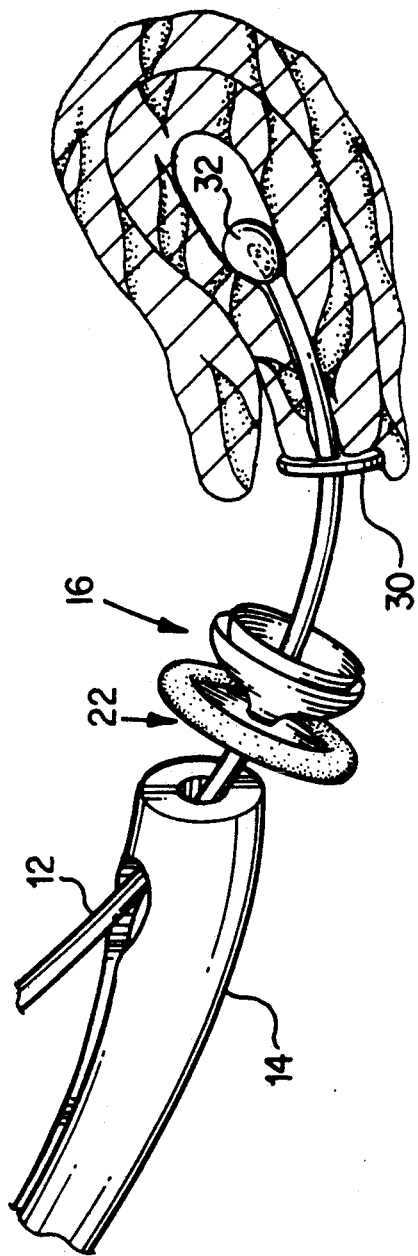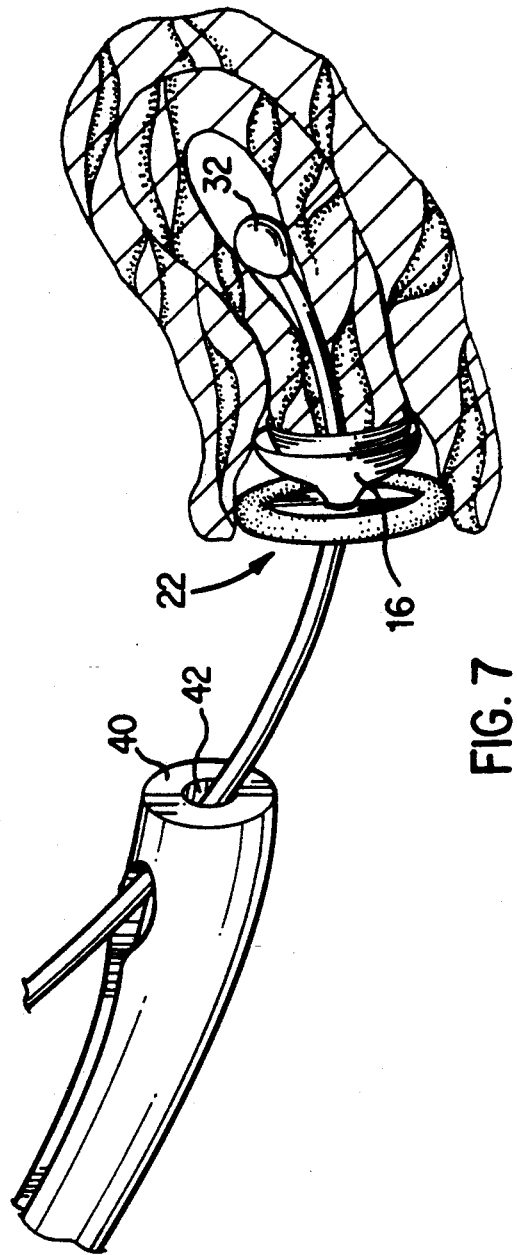

VAGINAL CERVICAL RETRACTOR ELEVATOR

BACKGROUND OF THE INVENTION

Various medical examinations and procedures which are performed on women require that the women's uterus be manipulated such that the uterus and cervix can be properly viewed by the physician. Typical of these examinations and procedures would be a complete total laparoscopic hysterectomy, a partial laparoscopic hysterectomy, a colpotomy, as well as other procedures and examinations. Generally, during the performance of a laparoscopic procedure, a small incision is made in the wall of the abdomen and a laparoscope is inserted therethrough to permit visualization of the peritoneal cavity and the uterus.

A number of instruments have been developed to assist the physician in visualizing the uterus and facilitating the performance of these various examinations and procedures. Typical of these prior art instruments are those which are described in U.S. Pat. Nos. 3,926,192 issued to Van Maren; 4,000,743 issued to Weaver; 4,976,717 issued to Boyle; and 4,997,419 issued to Lakatos et al. The patent to Van Maren is directed to a medical instrument which is inserted into the vagina and passes through the cervix to enter the uterus. A cup-shaped member is provided whose end wall is connected to a source of vacuum, the cup-shaped member including a conical element designed to be placed against the cervical os. The patent to Weaver describes a uterine anteverter which includes an arcuately curved shield which limits the distance a manipulating arm can be extended into the uterine cavity.

However, none of these prior art medical instruments adequately and completely perform its function so as to reduce the time of the surgical procedure, would minimize blood loss during surgery and would minimize the risk of infection and injury to the patient during surgery.

SUMMARY OF THE INVENTION

The present invention alleviates the problems of the prior art devices by providing a device which can perform a complete, total laparoscopic hysterectomy and other procedures such as a colpotomy while maintaining pneumoperitoneum, thereby preventing abdominal deflation once the vagina is entered during laparoscopic surgery, by utilizing a vaginal cervical retractor elevator provided with an inner plastic tubing, inner and outer caps designed to move on the inner tubing and a hollow, plastic outer shaft into which the inner tubing can be inserted. The outer cap is provided with a funnel-like base and both caps include a hole therein allowing a uterine manipulator to be inserted therethrough. When the vaginal cervical retractor elevator is inserted into the vagina, the inner cap surrounds and supports the cervix and the outer cap stretches the upper vaginal canal, allowing the manipulator to perform its particular procedure.

The present invention is best suited for surgical procedures requiring cervical uterine motions with elevation and retraction of the vaginal fornices, such as total laparoscopic hysterectomy, total abdominal hysterectomy, anterior pelvic peritoneal resection, culdesac resection or dissection such as in endometriosis. Furthermore, the present invention also assists in guiding the upper limit of the vaginal canal by retracting and elevating the vaginal fornix which would be helpful in the identification of the lower uterine segment. The device would also be of assistance if laparoscopic retropubic urethropexy for urinary stress incontinence by retracting the cervix at approximately the upper ⅓ of the vagina down into the posteria pelvis creating more space for urinary incontinence surgery in retzius space.

BRIEF DESCRIPTION OF THE DRAWINGS

These and other objects and advantages of the present invention will be described in conjunction with the accompanying drawings, in which:

FIG. 2 is a perspective view of the inner tube of the present invention;

FIG. 3 is a perspective view of the outer shaft of the present invention;

FIGS. 6, 7 and 8 are diagrammatic views of the present invention as it is inserted into the women's uterus.

DETAILED DESCRIPTION OF THE PREFERRED EMBODIMENT

Figure 1:
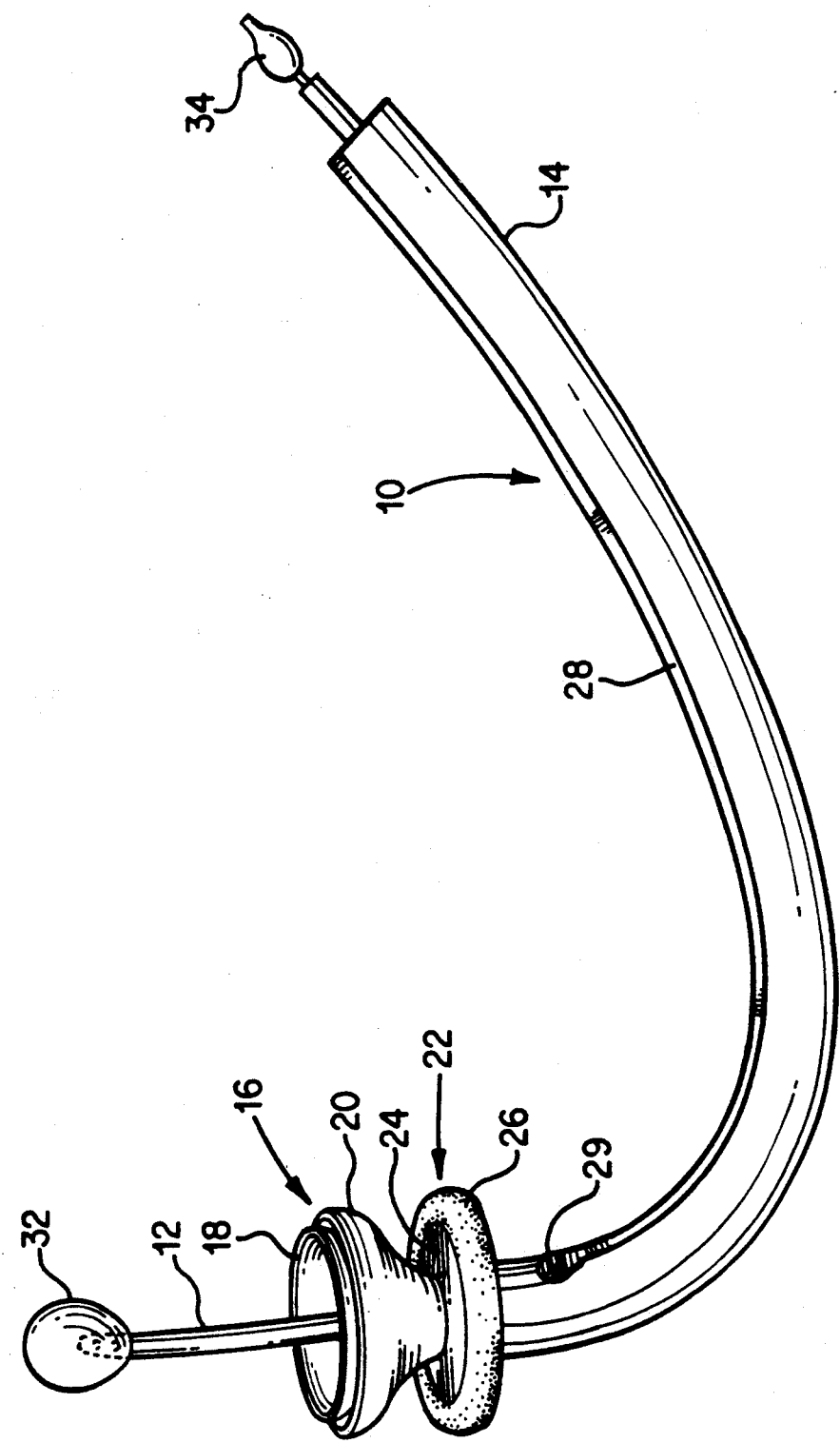
FIG. 1 is a perspective view of the present invention.
Figure 4:
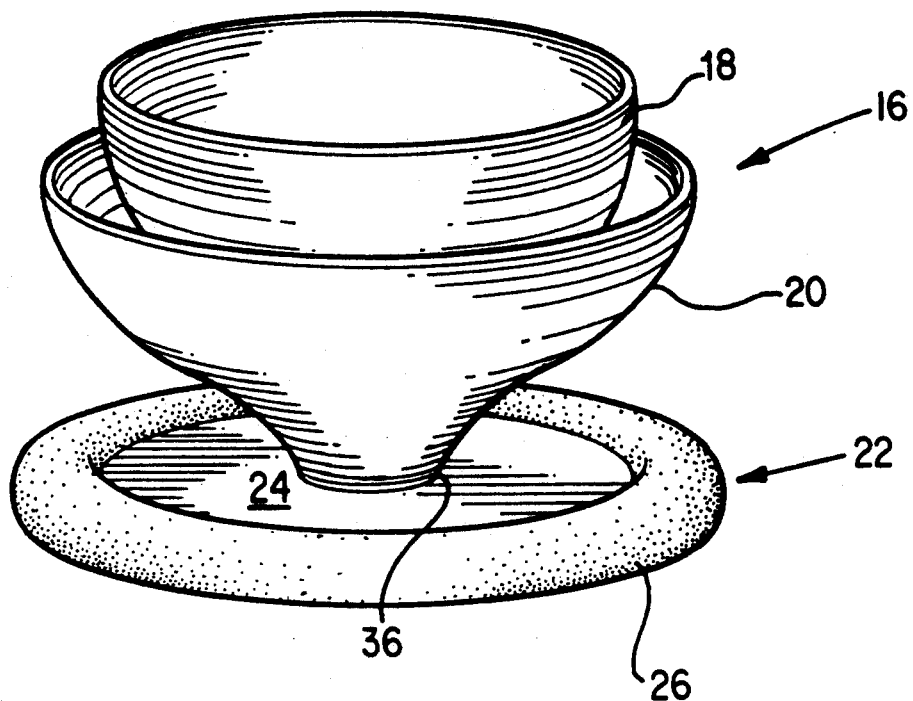
FIG. 4 is a plan view of the cervical caps and disks of the present invention.
Figure 5:
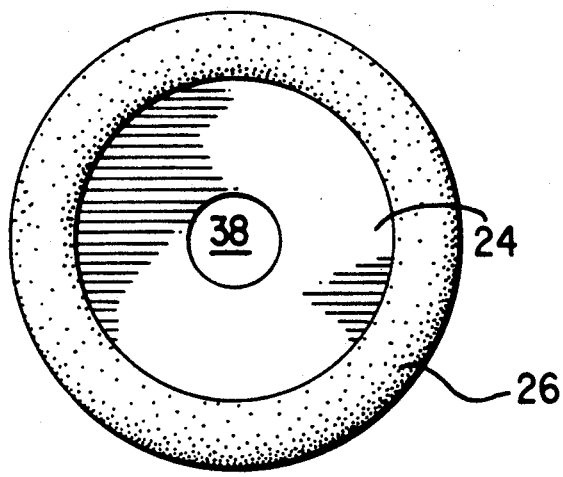
FIG. 5 is a top view of the disks shown in FIG. 4.

The present invention 10, as illustrated in FIGS. 1-5, consists of a hollow, plastic outer shaft 14 having a proximal-half-length curve corresponding to the curve of the posterior pelvis and a straight distal half which can be employed as a handle. A groove 28 is provided in the outer shaft 14 extending from the distal end to immediately prior to the proximal end of the shaft terminating with an elongated beaded aperture 29. An inner, plastic tube 12 can be mounted directly within the outer shaft 14 and snaps into the outer shaft which acts as a retaining cover and handle. A circular cervical disk 30 is permanently attached to the tube 12 at a distance of from 5-9 cm to the proximal end of the tube 12, based upon the physiological makeup of the patient. A vaginal cervical retractor elevator 16 consists of an inner cap 18 and an outer cap 20 which terminates with a funnel-shaped base 36. Each of the caps is provided with a hole therein so that it can slide on the inner tube 12. A circular disk 22 consisting of an inner disk 24 manufactured from a firm plastic material and an outer disk 26 made from a softer, more flexible plastic material is directly affixed to the funnel base 36 of the outer cap 20. A hole 38 is provided within the inner disk 24 to allow for movement on the inner tube 12. When the inner tube 12 is mounted on the shaft 14, the disk 22 is in direct contact with the shaft 14. In use, this disk 22 would make an airtight seal in the vagina to maintain pneumoperitoneum when a circumferential colpotomy is completed.

The inner tube 12 is provided with an intrauterine portion at a right angle with the shaft 14 to keep the uterus interverted. The proximal end of the tube 12 is provided with a balloon 32 which can be inflated up to approximately three cubic centimeters with air. The tube 12 communicates directly with the balloon 32 by a very fine, thin, inner lumen with the outer end of this tube 12 terminating in a balloon 34 with a luer lock. Air injected through the luer lock would inflate both of the balloons 32, 34. The balloon 34 which is at the end point of the tube 12 communicates with the balloon 32 at the opposite end of the tube. The balloon 32 is inserted inside the uterine cavity and is inflated to stay in place by injecting air through the balloon 34 which remains outside of the uterine cavity. Balloon 34 has a leur lock on it, which can be connected to an air filled syringe for inflation or deflation. The balloon 34 also transmits the pressure generated from the uterine cavity since it directly communicates with the balloon 32 and placed inside the uterine cavity. In other words, when balloon 34 is inflated with air, it inflates the balloon 32. Therefore, balloon 34 can also be used to determine the amount of tension in balloon 32. The balloon 32 of the tube 12 does not directly manipulate the uterine fundus and the total length of this tube can vary from between 30 to 36 cm. Similarly, based upon the physiology of the woman, including the size of the uterine cavity, the shaft 14 would measure approximately 24 to 30 cm. and would include a proximal end 40 having an opening 42 through which the inner tube 12 would extend.

The vaginal cervical retractor elevator 16 includes the inner cap 18 and outer cap 20 constructed in one piece and connected at the funnel base 36. Similar to the sizes of the tube 12 and the shaft 14, the diameter of the cap would vary based upon the physiology of the woman. The gap between the caps 18, 20 is approximately 2 mm and the outer cap 20 is approximately 2 mm below the inner cap 18, creating a space in the shape of a groove between these two caps which can be approximately 3 mm in depth. The diameter of the inner cap 18 would vary from 3 cm to 4 cm. Similarly, the depth of the inner cervical cap 18 would also vary from approximately 12 mm to 20 mm.

Figure 8:
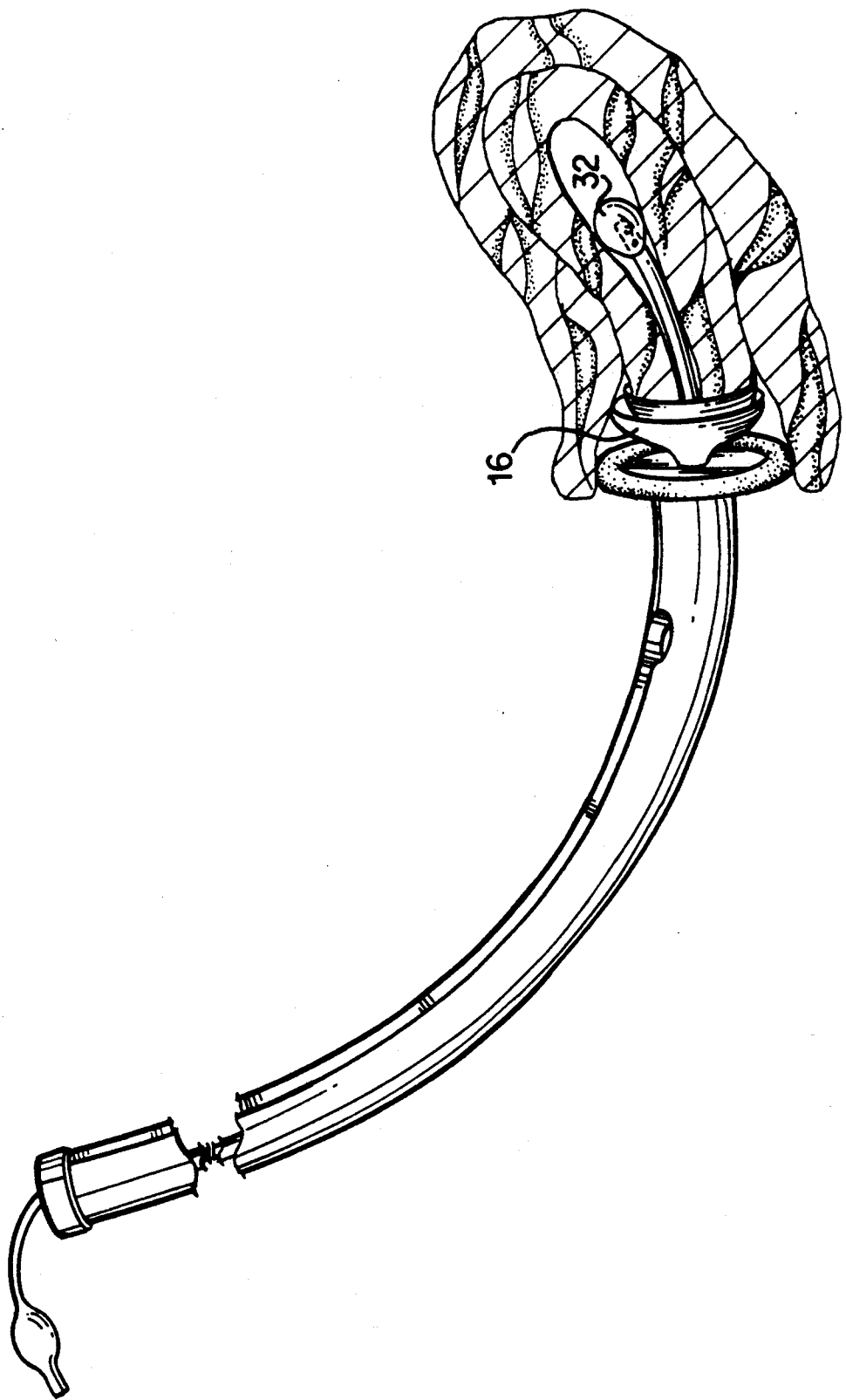

FIGS. 6-8 illustrate the method of inserting the vaginal cervical retractor elevator into a women's uterine cavity. Initially, the interior cervical lip is grasped with an Ellis clamp or a similar instrument with teeth, and the uterine cavity is measured. Based upon this particular uterine cavity measurement, a properly sized vaginal cervical retractor elevator and its corresponding inner tube 12 and outer shaft 14 would be utilized. Generally, the measurement of the cavity should be greater than 5 cm in depth. If a depth of less than 5 cm is measured, the cervical canal would be dilated with a dilator sufficient enough to accommodate a 5 mm diameter of the tube 12. The tube 12 is then inserted into the uterine cavity after the balloon 32 provided on the proximal end of the tube 12 is lubricated. The balloon 32 is then inflated using 7 to 8 cm of air from the luer lock. At this point, the cervical disk 30 will abut the external cervical os (see FIG. 6). The Ellis clamp from the cervical lip is then disconnected and the tube 12 with all its attachments is secured and properly connected with the uterus so that it will not be dislodged unless undue traction is applied. The loose, interchangeable vaginal cervical retractor elevator 16 connected with the tube 12 is pushed into the cervical canal and against the cervical disk 30. At this point, the widest diameter of the cap would be against the vaginal fornix (FIG. 7). The shaft 14 is then gently pushed into the vaginal canal, sliding over the tube 12 until it is in contact with the vaginal cervical retractor elevator 16. The tube 12 is then snapped into the hollow groove 28 (FIG. 8). At this point, the vaginal portion of the vaginal cervical retractor elevator 16 will be in the same parallel curve with that of the sacral hallow to give the maximum mobility to the cervix, and the upper portion of the vaginal canal. If the shaft 14 is pulled, the balloon 32 at the tip of tube 12 will retain the instrument connected with the uterine cavity. If the shaft 14 is inadvertently pushed at this point, the cervical disk 30 will prevent the tube 12 from injuring the uterine fundus.

The purpose of the present invention is to identify and retract the vaginal fornices around the cervix. When pushed up, the bladder and the bowel retract backward away from the upper ⅓ of the vagina and cervix. By doing this, a colpotomy can be safely performed after proper tissue dissection.

To perform an interior pelvic peritoneal dissection of the bladder flap, the shaft 14 is pushed along its axis and is pushed downward to the sacrum. This will retract the bladder over the anterior vaginal wall, and edges of the cap 16 would appear protruding and would be easily identifiable. The anterior peritoneal is cut in the usual fashion. The bladder is then dissected bluntly over the visible protrusion of the cervical cap up to approximately ⅛ inch to the edges of the cap. The bladder wall is loosely adherent to the isthmus of the uterus and anterior vaginal wall. At the edges of the cap 16, tissue is then picked up and dissected bluntly or sharply and the anterior colpotomy is then performed.

For a posterior colpotomy or culdesac dissection, the shaft 14 is again pushed up and lifted toward the anterior abdominal wall and away from the sacrum. This will result in protrusion of the edges of the cap 16 behind the uterus, and can be used for dissection and colpotomy formation.

In order to perform circumferential colpotomy, a total abdominal hysterectomy or a total laparoscopic hysterectomy, the shaft 14 is gently pushed inward and then lifted in the opposite direction to stretch and elevate the vaginal fornix by use of the cap 16. Colpotomy is started interiorly in a counterclockwise manner, by cutting and sliding within the groove 28 of the cap. A pure current monopolar hook is recommended for this use since the direct use of a carbon dioxide laser is counterindicated due to the presence of oxygen. Descending uterine vessels should be thoroughly desiccated prior to the formation of the circumferential colpotomy. During a culdesac dissection, when colpotomy is not needed, the cap 16 would help identify the recto vaginal septum.

When the present invention is used for a laparoscopic hysterectomy, the uterer must be secured and isolated. If a GIA multifier endoclip is applied medial to the cervical cap, it would escape the descending uterine branch, as it would when the cervical cap is not used. In this situation, the descending uterine branch must be desiccated with a bipolar cautery over the cap 16, before performing a circumferential colpotomy. If the GIA multifier is applied on the uterine vessels, lateral to the cap 16, it must be assured that the uterer is not clamped. This can very safely be done and is recommended provided that the ureter can be safely secured. In this situation, the ureteral peristalsis must be in the right direction and no ureteral distention must be noted. By doing so, the descending uterine branch would be more likely ligated.

It is important to know the uterine discoloration after uterine vasculature ligation, does not mean ligation of the descending branch of the uterine artery, which needs to be properly ligated or desiccated prior to the completion of the hysterectomy.

When bipolar desiccation is used for uterine vessels, the same principals apply. In this instance, after the uterer is being properly secured, isolated and visualized, the bladder benign properly dissected down, uterine vessels could be safely desiccated lateral to the uterus all the way down to the edges of the cap 16, and cut. Circumferential colpotomy can then be performed. Proper and thorough bipolar desiccation of the uterine vessels, prior to cutting, is very important to avoid any delayed or intraoperative bleeding. Monopolar or laser coagulation of an artery may result in bleeding and is not recommended.

In a retroverted uterus, the cardinal ligament is far too thick and long on the isthmus of the uterus. The uterus is rotated introverted with the rotation of the shaft 14. This tissue needs to be desiccated with bipolar coagulation and cut all the way down to the cap 16.

When the various procedures are completed, the vaginal cervical retractor elevator is removed by initially deflating the balloons 32 and 34. When the shaft 14 is pulled to remove the device, the disk 30 will pull the cervical vaginal cap 16 along with it.

While the device of the present invention has been described in connection with a particular type of surgical procedure, it should be understood that this instrument may be used in other situations where deliberate directing, movement and visualization of the uterus is required. Additionally, it is understood that various changes can be made by one possessing ordinary skill in the art which would be beyond the scope of protection.

What is claimed is:

1. A device for the manipulation of the uterus comprising:
   an elongated inner tube having a distal end and a proximal end;
   an outer cervical cap having a top portion of a first diameter and a bottom portion having a second diameter less than said first diameter, said bottom portion of said outer cap provided with a hole therein;
   an inner cervical cap having a top portion of a third diameter and a bottom portion having a fourth diameter less than said third diameter, said bottom portion of said inner cap provided with a hole therein, said inner cap joined to, and provided within said outer cap to form a retractor elevator, said elevator movable on said elongated inner tube; and
   an outer hollow shaft having a distal end and a proximal end, provided with a longitudinal groove having a distal end and a proximal end extending from the distal end of said outer shaft to immediately prior to the proximal end of said shaft, said elongated inner tube inserted into said outer shaft during uterine manipulation;
   wherein when said device is utilized, said inner cap would surround and support the cervix and said outer cap would stretch the upper vaginal canal.

2. The device in accordance with claim 1, wherein said longitudinal groove terminates at its proximal end with an elongated beaded aperture, the proximal end of said outer hollow shaft provided with a hole enabling said inner tube to move through said beaded aperture and said hole of said outer hollow shaft.

3. The device in accordance with claim 1, further including a disk provided with a hole therein, said disk attached to said bottom portion of said outer cap.

4. The device in accordance with claim 3, wherein said disk is provided with an inner disk made from a firm plastic material and an outer disk, surrounding said inner disk, made from a softer, more flexible plastic material.

5. The device in accordance with claim 3, wherein a cervical stop is permanently affixed to said elongated inner tube close to its proximal end.

6. The device in accordance with claim 5, wherein the proximal end of said inner tube is provided with a first balloon and the distal end of said inner tube is provided with a second balloon.

7. The device in accordance with claim 1, wherein a cervical stop is permanently affixed to said elongated inner tube close to its proximal end.

8. The device in accordance with claim 7, wherein the proximal end of said inner tube is provided with a first balloon and the distal end of said inner tube is provided with a second balloon.

9. The device in accordance with claim 1, wherein the proximal end of said inner tube is provided with a first balloon and the distal end of said inner tube is provided with a second balloon.

* * * * *